(12) United States Patent
You et al.

(10) Patent No.: US 10,119,065 B2
(45) Date of Patent: Nov. 6, 2018

(54) COMPOSITION FOR FRACTURING AND DISPLACEMENT AND METHOD FOR FRACTURING AND DISPLACEMENT OF TIGHT OIL RESERVOIR

(71) Applicants: China University of Geosciences (Beijing), Beijing (CN); China University of Petroleum(East China), Qingdao, Shandong (CN)

(72) Inventors: Qing You, Beijing (CN); Caili Dai, Qingdao (CN); Yan Zhang, Beijing (CN); Mingwei Zhao, Qingdao (CN); Yining Wu, Qingdao (CN); Guang Zhao, Qingdao (CN); Yongpeng Sun, Qingdao (CN); Huan Wang, Beijing (CN); Yifei Liu, Qingdao (CN); Jichao Fang, Qingdao (CN)

(73) Assignees: China University of Geosciences (Beijing) (CN); China University of Petroleum (East China) (CN)

(*) Notice: Subject to any disclaimer, the term of this patent is extended or adjusted under 35 U.S.C. 154(b) by 0 days.

(21) Appl. No.: 15/668,900

(22) Filed: Aug. 4, 2017

(65) Prior Publication Data
US 2018/0237684 A1  Aug. 23, 2018

(30) Foreign Application Priority Data

Feb. 21, 2017 (CN) .......................... 2017 1 0093083

(51) Int. Cl.
*C09K 8/68* (2006.01)
*C07D 207/325* (2006.01)
*C09K 8/86* (2006.01)

(52) U.S. Cl.
CPC ............ *C09K 8/68* (2013.01); *C07D 207/325* (2013.01); *C09K 8/86* (2013.01)

(58) Field of Classification Search
CPC .............................. C09K 8/68; C07D 207/325
See application file for complete search history.

(56) References Cited

U.S. PATENT DOCUMENTS

| 2009/0181865 A1* | 7/2009 | Dessinges | C09K 8/64 |
| | | | 507/202 |
| 2011/0071056 A1* | 3/2011 | Saini | C09K 8/035 |
| | | | 507/119 |

(Continued)

OTHER PUBLICATIONS

Interaction between asphaltene and quartz surface and mechanisms of wettability alteraction, Chinese Journal of Petroleum Geology and Recovery Efficiency; vol. 18, No. 4, Jul. 2011, with English abstract.

(Continued)

*Primary Examiner* — Alicia Bland
(74) *Attorney, Agent, or Firm* — Calfee, Halter & Griswold LLP

(57) ABSTRACT

The present invention relates to the field of oilfield chemistry, and discloses a composition for fracturing and displacement and a method for fracturing and displacement of a tight oil reservoir. The composition contains a pyrrolic compound represented by formula (1) and a laurate; in the formula (1), $M^-$ is halide ion, $R_1$ is C1-C5 linear or branched alkyl, and $R_2$ is C15-C20 linear or branched alkyl. The composition for fracturing and displacement provided in the present invention has functions of fracturing, solid carrying, imbibition, drainage and oil displacement, so as to maximize the recovery efficiency of tight oil, and attain economic and social benefits by implementing multiple functions with a single composition, saving resources, and reducing cost.

(Continued)

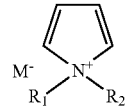

formula (1)

4 Claims, 5 Drawing Sheets

(56) References Cited

U.S. PATENT DOCUMENTS

| | | | |
|---|---|---|---|
| 2015/0148266 A1* | 5/2015 | Webber | C09K 8/52 507/90 |
| 2016/0060504 A1* | 3/2016 | Dawson | C09K 8/584 166/300 |

OTHER PUBLICATIONS

Experimental study of spontaneous imbibition in low permeability core, fractured reservoir, Chinese Journal of Petroleum Geology and Recovery Efficiency; vol. 18, No. 5, Sep. 2011, with English abstract.

\* cited by examiner

COMPOSITION FOR FRACTURING AND DISPLACEMENT AND METHOD FOR FRACTURING AND DISPLACEMENT OF TIGHT OIL RESERVOIR

CROSS REFERENCE TO RELATED APPLICATIONS

This application claims priority to Chinese Application No. 201710093083.7, filed on Feb. 2, 2017, entitled "Fracturing and Displacement Fluid for Tight Oil Reservoir and Preparation Method Thereof", which is specifically and entirely incorporated by reference.

FIELD OF THE INVENTION

The present invention relates to the field of oilfield chemistry, in particular to a composition for fracturing and displacement and a method for fracturing and displacement of a tight oil reservoir.

BACKGROUND OF THE INVENTION

Tight oil resources are abundant in China. It is estimated that the total reserve of exploitable tight oil resources is about 1.4-2 billion tons, and the exploitation potential is huge. The successful exploitation of two major tight oil fields—Chang 7 Oil Field in Erdos and Jimusar Oil Field in Jungar Basin—indicates that tight oil will become fresh blood for crude oil supply in China. However, the tight oil reservoirs in China usually have porosity lower than 10% and permeability lower than $0.1 \times 10^{-3}$ $\mu m^2$, i.e., have typical characteristics of low porosity and low permeability. The reservoir throats have a prominent characteristic of micro-nanoscale pore throat system. For example, the throat radius of the tight oil reservoirs in Chang 7 Oil Field in Erdos Basin is mainly distributed in a range of 0.10-0.75 μm. Therefore, when manual fracturing measures are used and the solids carried by the fracturing fluid are utilized to form a manual fracture network system in the reservoir for depletion-drive development, it is difficult to displace the crude oil in the matrix to the fracture network because the matrix is tight, and the fracture network will close and block the oil streams as the reservoir pressure is decreased. That is the principal cause for rapid decline of production and low recovery efficiency in depletion-drive development, and difficulties in subsequent energy replenishment. Usually, the annual decline of production of tight oil is >40%, or even as high as 90%; the average primary recovery efficiency of tight oil is as low as 5%-10%. To further improve the recovery efficiency of tight oil, the producing energy may be replenished with stimulation measures, such as injection of displacement fluid, gas, or water, etc. Though the recovery efficiency can be improved by water injection, it is difficult to inject water, a hydrated film may be formed easily on the rock surfaces of the tight oil reservoir owing to polarity. The clay minerals in the formation tend to swell and the pores tend to close when the clay minerals encounter water, resulting in rapid increase of injection pressure and severe reduction of injected volume; consequently, the producing energy can't be replenished effectively. Large-scale application of gas injection is limited owing to the problem of gas source.

SUMMARY OF THE INVENTION

To overcome the drawback of low recovery efficiency of tight oil in the prior technics, the present invention provides a composition for fracturing and displacement and a method for fracturing and displacement of a tight oil reservoir. The composition for fracturing and displacement provided in the present invention has functions of fracturing, solid carrying, imbibition, drainage and oil displacement, so as to maximize the recovery efficiency of tight oil, and attain economic and social benefits by implementing multiple functions with a single composition, saving resources, and reducing cost.

In one aspect, the present invention provides a composition for fracturing and displacement, which contains a pyrrolic compound represented by formula (1) and a laurate;

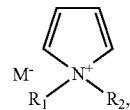

formula (1)

where, $M^-$ is halide ion, $R_1$ is C1-C5 linear or branched alkyl, and $R_2$ is C15-C20 linear or branched alkyl.

In another aspect, the present invention provides a method for fracturing and displacement of a tight oil reservoir, which comprises: injecting a fracturing and displacement fluid into the tight oil reservoir, wherein, the fracturing and displacement fluid is a water solution that contains the pyrrolic compound represented by formula (1) and the laurate according to the present invention.

The present invention attains the following beneficial effects:

(1) The composition for fracturing and displacement provided in the present invention has the solid-carrying function of a fracturing fluid and the imbibition, drainage and oil displacement functions of a surfactant, attains $10^{-3}$ mN/m ultra-low interfacial tension with the crude oil after viscosity breaking, implements multiple functions, and greatly reduces the input cost in an oil field.

(2) The composition for fracturing and displacement in the present invention is environment friendly and has low requirements for equipment. It can be applied through a simple process. It can greatly simplify the field operation procedures and reduces input cost. It can combine fracturing and oil displacement operations into one operation.

(3) The composition for fracturing and displacement provided in the present invention is applicable to fracturing and displacement of medium and high temperature tight oil reservoirs within 40-90° C. temperature range, and has wide applicability.

(4) The composition for fracturing and displacement provided in the present invention doesn't require flowback after fracturing; instead, it can be directly used for imbibition, drainage and oil displacement after viscosity breaking in crude oil or water, and thereby avoiding environmental pollution resulted from flowback fluid, which eliminating flowback fluid processing cost changing wastes into valuables.

DETAILED DESCRIPTION

Figure 1:
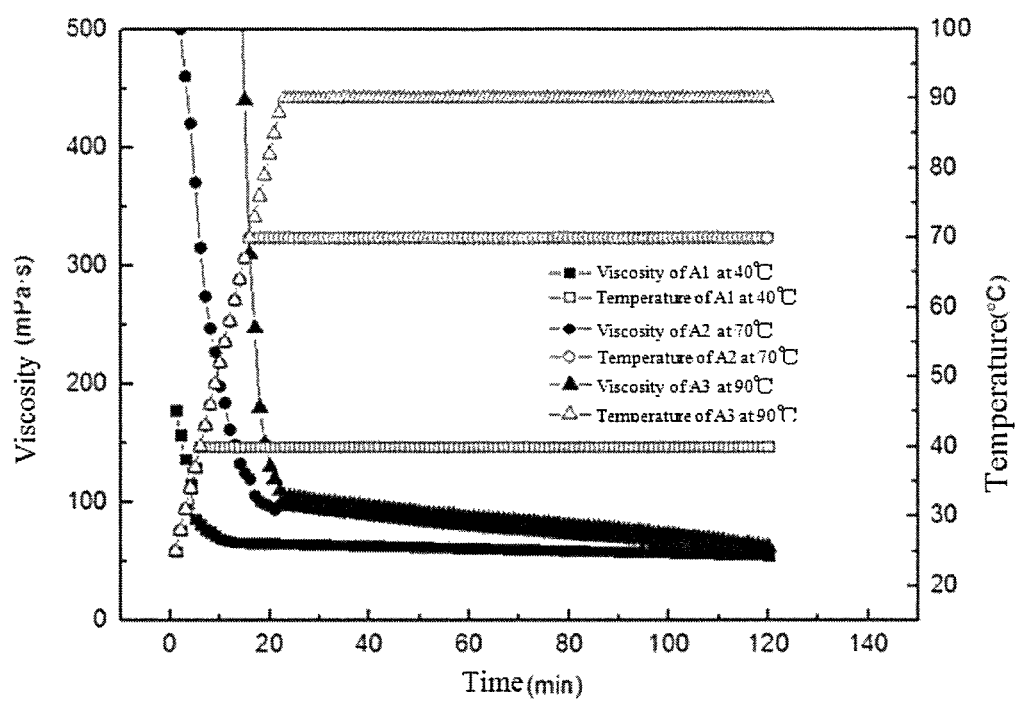
FIG. 1 shows the temperature-resistant and shear-resistant properties of the fracturing and displacement fluid in examples 1-3 of the present invention.

The ends points and any value in the ranges disclosed in the present invention are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically in this document.

In one aspect, the present invention provides a composition for fracturing and displacement, which contains a pyrrolic compound represented by formula (1) and laurate;

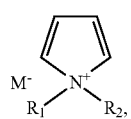

formula (1)

where, $M^-$ is halide ion (e.g., chloride ion, bromine ion, fluoride ion, or iodine ion), $R_1$ is C1-C5 linear or branched alkyl (e.g., methyl, ethyl, n-propyl, iso-propyl, n-butyl, iso-butyl, tert-butyl, n-pentyl, tert-pentyl, and neo-pentyl), and $R_2$ is C15-C20 linear or branched alkyl (e.g., C15 alkyl, C16 alkyl, C17 alkyl, C18 alkyl, C19 alkyl, and C20 alkyl).

In the present invention, preferably $R_1$ is C1-C3 linear chain linear or branched alkyl, further preferably is methyl; $R_2$ is C17-C19 linear alkyl, further preferably is octadecyl; more preferably, $M^-$ is bromine ion, $R_1$ is methyl, and $R_2$ is octadecyl. In that preferred embodiment, the composition has better fracturing and displacement performance.

In the present invention, to further improve the fracturing and displacement performance of the composition, preferably, the weight ratio of the pyrrolic compound and the laurate contained in the composition is 0.5-20:1, further preferably is 1-6:1.

According to a preferred embodiment of the present invention, the composition for fracturing and displacement is in a form of water solution.

Preferably, in the water solution, the content of the pyrrolic compound is 0.5-10 wt % (e.g., 0.5 wt %, 1 wt %, 1.5 wt %, 2 wt %, 2.5 wt %, 3 wt %, 3.5 wt %, 4 wt %, 4.5 wt %, 5 wt %, 5.5 wt %, 6 wt %, 6.5 wt %, 7 wt %, 7.5 wt %, 8 wt %, 8.5 wt %, 9 wt %, 9.5 wt %, or 10 wt %), preferably is 2-7 wt %; the content of the laurate is 0.1-2 wt % (e.g., 0.1 wt %, 0.15 wt %, 0.2 wt %, 0.25 wt %, 0.3 wt %, 0.35 wt %, 0.4 wt %, 0.45 wt %, 0.5 wt %, 0.55 wt %, 0.6 wt %, 0.65 wt %, 0.7 wt %, 0.75 wt %, 0.8 wt %, 0.85 wt %, 0.9 wt %, 0.95 wt %, 1 wt %, 1.05 wt %, 1.1 wt %, 1.15 wt %, 1.2 wt %, 1.25 wt %, 1.3 wt %, 1.35 wt %, 1.4 wt %, 1.45 wt %, 1.5 wt %, 1.55 wt %, 1.6 wt %, 1.65 wt %, 1.7 wt %, 1.75 wt %, 1.8 wt %, 1.85 wt %, 1.9 wt %, 1.95 wt %, or 2 wt %), preferably is 0.5-1.75 wt %; the content of water is 88-99.4 wt % (e.g., 88 wt %, 88.5 wt %, 89 wt %, 89.5 wt %, 90 wt %, 91.25 wt %, 91.5 wt %, 92 wt %, 92.5 wt %, 93 wt %, 93.5 wt %, 94 wt %, 94.5 wt %, 95.5 wt %, 96 wt %, 96.5 wt %, 97 wt %, 97.5 wt %, 98 wt %, 98.5 wt %, 99 wt %, or 99.4 wt %), preferably is 91.25-97.5 wt %.

In the present invention, the laurate may be any existing laurate that is dissoluble in water; for example, the laurate may be sodium laurate and/or potassium laurate.

In a preferred embodiment of the present invention, the water used in a process for forming the water solution contains $Na^+$, $K^+$, $Ca^{2+}$, $Mg^{2+}$, $HCO_3^-$ and $Cl^-$, wherein, the total concentration of $K^+$ and $Na^+$ is 1,000 to 100,000 mg/L, further preferably is 1,000 to 50,000 mg/L; the total concentration of $Ca^{2+}$ and $Mg^{2+}$ is 10 to 5,000 mg/L, further preferably is 10 to 3,000 mg/L. In that preferred embodiment, the composition has better fracturing and oil displacement performance.

In the present invention, there is no particular restriction on the concentrations of $HCO_3^-$ and $Cl^-$ in the water, and $HCO_3^-$ and $Cl^-$ may coexist with cations correspondingly; for example, the concentration of $HCO_3^-$ is 20 to 2,000 mg/L, further preferably is 20 to 1,000 mg/L, the concentration of $Cl^-$ is 1,000 to 110,000 mg/L, further preferably is 1,000 to 55,000 mg/L.

In another aspect, the present invention provides a method for fracturing and displacement of a tight oil reservoir, which comprises: injecting a fracturing and displacement fluid into the tight oil reservoir, wherein, the fracturing and displacement fluid is a water solution that contains the pyrrolic compound represented by formula (1) and the laurate according to the present invention.

The water solution is as that described above, and will not be further detailed here.

In the present invention, to select an appropriate fracturing and displacement fluid according to specific formation conditions conveniently, preferably the method for preparation of the water solution comprises: mixing the pyrrolic compound with the laurate, and then mixing the obtained mixture with water. The processing of mixing the mixture with water may be executed on the construction site; specifically, the mixture may be diluted with water to required concentration on the site while it is agitated, according to the requirement for the concentration on the site.

In the present invention, preferably, the temperature of the tight oil reservoir is 40-90° C. The method for fracturing and displacement in the present invention attains a better effect of fracturing and displacement of the tight oil reservoir within that temperature range.

In the present invention, to improve the performance of the water solution in a tight oil reservoir at different temperatures and attain a better effect of fracturing and displacement, preferably, when the temperature of the tight oil reservoir is 40-60° C., based on the water solution, the content of the pyrrolic compound is 1-3 wt %, and content of the laurate is 0.5-0.9 wt %; when the temperature of the tight oil reservoir is 60-75° C., based on the water solution, the content of the pyrrolic compound is 3-5 wt %, and the content of the laurate is 0.9-1.4 wt %, when the temperature of the tight oil reservoir is 75-90° C., based on the water solution, the content of the pyrrolic compound is 5-7 wt %, and the content of the laurate is 1.4-1.75 wt %.

In the present invention, the method for preparation of the pyrrolic compound represented by formula (1) may be: a compound represented by formula (2) and a compound represented by formula (3) are subjected to react in the presence of methylene chloride.

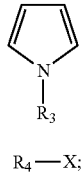

formula (2)

$R_4—X;$ formula (3)

where, the $R_3$ in formula (2) is the same as the $R_1$ in formula (1), the $R_4$ in formula (3) is the same as the $R_2$ in formula (1), and the X in formula (3) is the same as the M in formula (1).

In the present invention, the weight ratio of the amount of the compound represented by formula (2) and the amount of methylene chloride is 0.08-0.09:1; the weight ratio of the compound represented by formula (3) and the methylene chloride is 0.45-0.55:1.

In the present invention, the conditions of the reaction may include: reaction temperature of 80-90° C. and reaction time of 40-50 h. Preferably, the reaction is executed under nitrogen protection.

In the present invention, after the reaction is finished, the superfluous methylene chloride in the solution is removed, to obtain a crude product. The method for removing the methylene chloride may be an existing method. For example, a rotary evaporation may be used to remove the superfluous methylene chloride.

In the present invention, the crude product is recrystallized and vacuum-dried to obtain the pyrrolic compound represented by formula (1). The solvent used in the recrystallization process may be ethyl acetate. The conditions of the vacuum drying preferably include: drying temperature of 25-50° C. and drying time of 1-4 h.

Hereunder the present invention will be detailed in embodiments. In the following embodiments, the prepared composition for fracturing and displacement is abbreviated as a fracturing and displacement fluid;

N-methyl-N-octadecyl-1H-pyrrolium bromide is prepared with the following method: 8.1 g methyl pyrrole and 49.95 g octadecyl bromide are mixed and loaded into a 500 mL three-neck flask, 100 g methylene chloride is added into the three-neck flask, nitrogen is charged into the three-neck flask for protection, and the mixture is heated up to 80° C. and controlled for reflux reaction for 48 h. After the reaction is finished, the superfluous methylene chloride is removed by rotary evaporation, the obtained crude product is recrystallized with ethyl acetate for four times, and then the product is vacuum-dried at 30° C. for 2 h, to obtain 1-methyl-4-octadecyl-1H-pyrrolium bromide.

N-methyl-N-octadecyl-1H-pyrrolium chloride is prepared with the following method: the above method for preparation of N-methyl-N-octadecyl-1H-pyrrolium bromide is used, but octadecyl chloride in the same weight is used to replace the octadecyl bromide.

N-n-propyl-N-octadecyl-1H-pyrrolium bromide is prepared with the following method: the above method for preparation of N-methyl-N-octadecyl-1H-pyrrolium bromide is used, but n-propyl pyrrole in the same weight is used to replace the methyl pyrrole.

N-methyl-N-pentadecyl-1H-pyrrolium bromide is prepared with the following method: the above method for preparation of N-methyl-N-octadecyl-1H-pyrrolium bromide is used, but pentadecyl bromide in the same weight is used to replace the octadecyl bromide.

Sodium laurate with trade name S103038-50 g from Shanghai Aladdin Biochemical Technology Co., Ltd. is used.

Example 1

2 g N-methyl-N-octadecyl-1H-pyrrolium bromide (in formula (1), $M^-$ is bromine ion, $R_1$ is methyl, and $R_2$ is octadecyl) and 0.5 g sodium laurate are mixed to obtain a mother liquid, and then 97.5 g water is added into the mother liquid while the mixture is stirred (the total concentration of $K^+$ and $Na^+$ in the water is 1493.81 mg/L, the total concentration of $Ca^{2+}$ and $Mg^{2+}$ is 77.69 mg/L, the concentration of $HCO_3^-$ is 325.37 mg/L, and the concentration of $Cl^-$ is 2278.75 mg/L). Thus, a fracturing and displacement fluid A1 is obtained.

Example 2

4 g N-methyl-N-octadecyl-1H-pyrrolium bromide (in formula (1), $M^-$ is bromine ion, $R_1$ is methyl, and $R_2$ is octadecyl) and 1 g sodium laurate are mixed to obtain a mother liquid, and then 95 g water is added into the mother liquid while the mixture is stirred (the total concentration of $K^+$ and $Na^+$ in the water is 3,623.75 mg/L, the total concentration of $Ca^{2+}$ and $Mg^{2+}$ is 228.10 mg/L, the concentration of $HCO_3^-$ is 395.98 mg/L, and the concentration of $Cl^-$ is 5,777.50 mg/L). Thus, a fracturing and displacement fluid A2 is obtained.

Example 3

7 g N-methyl-N-octadecyl-1H-pyrrolium bromide (in formula (1), M is bromine ion, $R_1$ is methyl, and $R_2$ is octadecyl) and 1.75 g sodium laurate are mixed to obtain a mother liquid, and then 91.25 g water is added into the mother liquid while the mixture is stirred (the total concentration of $K^+$ and $Na^+$ in the water is 7,100.88 mg/L, the total concentration of $Ca^{2+}$ and $Mg^{2+}$ is 449.02 mg/L, the concentration of $HCO_3^-$ is 572.54 mg/L, and the concentration of $Cl^-$ is 11,533.72 mg/L). Thus, a fracturing and displacement fluid A3 is obtained.

Example 4

The method described in the example 1 is used to prepare a fracturing and displacement fluid, but N-methyl-N-octadecyl-1H-pyrrolium chloride in the same weight is used to replace N-methyl-N-octadecyl-1H-pyrrolium bromide. Thus, a fracturing and displacement fluid A4 is obtained.

Example 5

The method described in the example 1 is used to prepare a fracturing and displacement fluid, but N-n-propyl-N-octadecyl-1H-pyrrolium bromide in the same weight is used to replace N-methyl-N-octadecyl-1H-pyrrolium bromide. Thus, a fracturing and displacement fluid A5 is obtained.

Example 6

The method described in the example 1 is used to prepare a fracturing and displacement fluid, but N-methyl-N-pentadecyl-1H-pyrrolium bromide in the same weight is used to replace N-methyl-N-octadecyl-1H-pyrrolium bromide. Thus, a fracturing and displacement fluid A6 is obtained.

Example 7

The method described in the example 1 is used to prepare a fracturing and displacement fluid, but the amount of N-methyl-N-octadecyl-1H-pyrrolium bromide is 15 g, and the amount of water is 84.5 g. Thus, a fracturing and displacement fluid A7 is obtained.

Example 8

The method described in the example 1 is used to prepare a fracturing and displacement fluid, but the amount of sodium laurate is 5 g, and the amount of water is 93 g. Thus, a fracturing and displacement fluid A8 is obtained.

Example 9

The method described in the example 1 is used to prepare a fracturing and displacement fluid, but the total concentration of $K^+$ and $Na^+$ in the water is 500 mg/L. Thus, a fracturing and displacement fluid A9 is obtained.

Example 10

The method described in the example 1 is used to prepare a fracturing and displacement fluid, but the total concentration of $Ca^{2+}$ and $Mg^{2+}$ in the water is 6,000 mg/L. Thus, a fracturing and displacement fluid A10 is obtained.

Test Cases (1) Test of Temperature-Resistant and Wear-Resistant Properties of the Fracturing and Displacement Fluids The viscosity of the fracturing and displacement fluid A1 sheared at 170 $s^{-1}$ shearing rate for 2 h at 40° C. is measured with a rheometer (from Thermo Fisher SCIENTIFIC, with trade name Haake MARS 60, the same below). The result is shown in FIG. 1 and Table 1;

The viscosity of the fracturing and displacement fluid A2 sheared at 170 $s^{-1}$ shearing rate for 2 h at 70° C. is measured with the rheometer. The result is shown in FIG. 1 and Table 1;

The viscosity of the fracturing and displacement fluid A3 sheared at 170 $s^{-1}$ shearing rate for 2 h at 90° C. is measured with the rheometer. The result is shown in FIG. 1 and Table 1;

The viscosity values of the fracturing and displacement fluids A4-A10 sheared at 170 $s^{-1}$ shearing rate for 2 h at 40° C. are measured with the rheometer respectively. The results are shown in Table 1.

(2) Test of Viscoelasticity of the Fracturing and Displacement Fluids

The viscoelasticity of the fracturing and displacement fluid A1 at 40° C. is measured with a rheometer (from Thermo Fisher SCIENTIFIC, with trade name Haake MARS 60, the same below), and the result is shown in FIG. 1;

The viscoelasticity of the fracturing and displacement fluid A2 at 70° C. is measured with the rheometer, and the result is shown in FIG. 1;

The viscoelasticity of the fracturing and displacement fluid A3 at 90° C. is measured with the rheometer, and the result is shown in FIG. 1.

(3) Test of Solid-Carrying Ability of the Fracturing and Displacement Fluids

Figure 3:
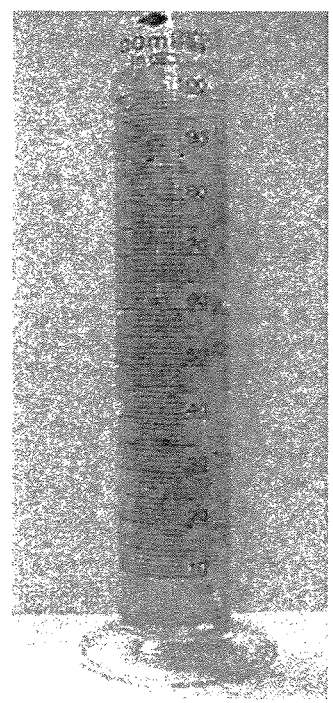
FIG. 3 shows the solid-carrying ability of the fracturing and displacement fluid in example 1 of the present invention.

The solid-carrying ability of the fracturing and displacement fluids A1-A10 is measured with a falling ball method through the following operations: (1) the prepared fracturing fluids A1-A10 are mixed intensively with 50 mesh ceramsites at 250 g/L solid concentration; (2) 100 mL sample is taken from the obtained mixture and loaded into a 100 mL graduated flask, and then the graduated flask is sealed, kept at room temperature (25° C.), and observed; (3) the height of ceramsites deposited on the bottom of the graduated flask is recorded once every half hour, and the sedimentation velocity is calculated (sedimentation velocity=height of deposited ceramsites/sedimentation time); (4) the step (3) is repeated for 4 times, till 2 h is passed; then, the average sedimentation velocity of the ceramsites is calculated. The test result of the fracturing and displacement fluid A1 is shown in FIG. 3 and Table 1; the test results of the fracturing and displacement fluids A2-A10 are shown in Table 1.

(4) Viscosity of the Solutions of the Fracturing and Displacement Fluids after Viscosity Breaking The fracturing and displacement fluids A1 and A4-A10 are mixed with crude oil at different mix ratios for 2 h at 40° C. respectively, and then the viscosity values of the solutions are obtained respectively; the results are shown in Table 1;

The fracturing and displacement fluids A1 and A4-A10 are mixed with water at different mix ratios for 2 h at 40° C. respectively, and then the viscosity values of the solutions are obtained respectively; the results are shown in Table 1;

The fracturing and displacement fluids A2 is mixed with crude oil at different mix ratios for 2 h at 70° C. respectively, and then the viscosity values of the solutions are obtained respectively; the results are shown in Table 1;

The fracturing and displacement fluids A2 is mixed with water at different mix ratios for 2 h at 70° C. respectively, and then the viscosity values of the solutions are obtained respectively; the results are shown in Table 1;

The fracturing and displacement fluids A3 is mixed with crude oil at different mix ratios for 2 h at 90° C. respectively, and then the viscosity values of the solutions are obtained respectively; the results are shown in Table 1;

The fracturing and displacement fluids A3 is mixed with water at different mix ratios for 2 h at 90° C. respectively, and then the viscosity values of the solutions are obtained respectively; the results are shown in Table 1.

Figure 4:
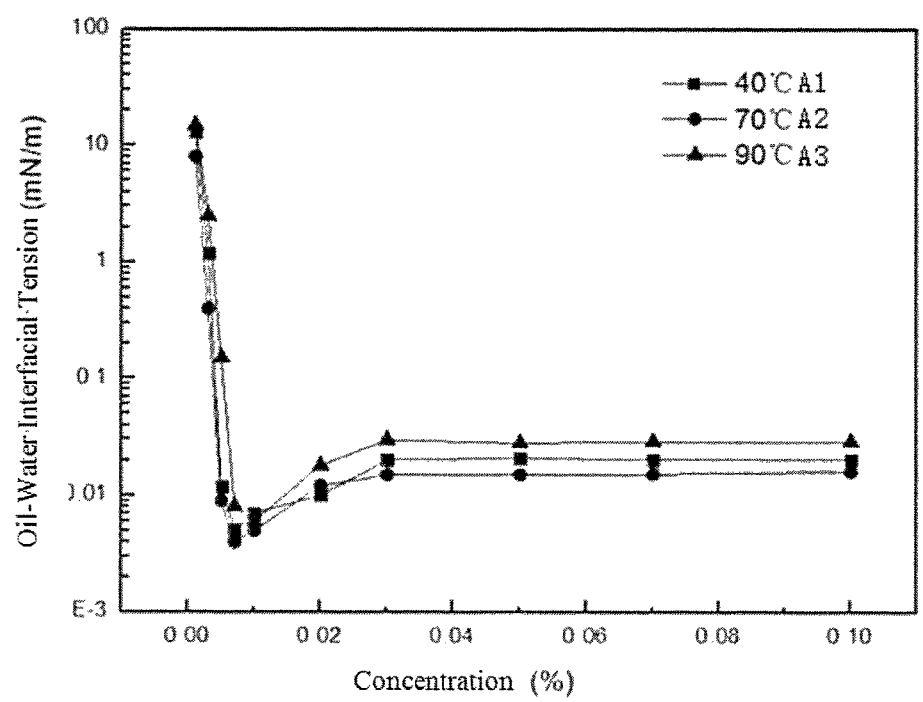
FIG. 4 shows the oil-water interfacial tension of the solution of the fracturing and displacement fluid in examples 1-3 of the present invention after viscosity breaking.

(5) Oil-Water Interfacial Tension of the Solutions of the Fracturing and Displacement Fluids after Viscosity Breaking With reference to the oil and natural gas industry standard "Method for Measurement of Surface Tension and Interfacial Tension", the solutions obtained by respectively mixing the fracturing and displacement fluids A1 and A4-A10 with water at 1:3 volume ratio at 40° C. for viscosity breaking are diluted to different concentrations (0.005 wt %, 0.01 wt %, 0.02 wt %, 0.05 wt %, and 0.10 wt %, the same below), and the interfacial tensions between the dilute solution and dehydrated and degassed crude oil (with 0.876 g/cm³ density and 8.8 mPa·s viscosity at 20° C.) are measured with a spinning drop interfacial tensiometer (from CNG USA Co., with trade name Texas-500C, the same below); the oil-water interfacial tension of the dilute solution of fracturing and displacement fluid A1 after viscosity breaking is shown in FIG. 4 and Table 2, and the oil-water interfacial tensions of the dilute solutions of fracturing and displacement fluid A4-10 after viscosity breaking are shown in Table 2;

With reference to the oil and natural gas industry standard "Method for Measurement of Surface Tension and Interfacial Tension", the solution obtained by mixing the fracturing and displacement fluids A2 with water at 1:3 volume ratio at 70° C. for viscosity breaking is diluted to different concentrations, and the interfacial tension between the dilute solution and dehydrated and degassed crude oil (with 0.876 g/cm$^3$ density and 8.8 mPa·s viscosity at 20° C.) is measured with the spinning drop interfacial tensiometer; the results are shown in FIG. 4 and Table 2;

With reference to the oil and natural gas industry standard "Method for Measurement of Surface Tension and Interfacial Tension", the solution obtained by mixing the fracturing and displacement fluids A3 with water at 1:3 volume ratio at 90° C. for viscosity breaking is diluted to different concentrations, and the interfacial tension between the dilute solution and dehydrated and degassed crude oil (with 0.876 g/cm$^3$ density and 8.8 mPa·s viscosity at 20° C.) is measured with the spinning drop interfacial tensiometer; the results are shown in FIG. 4 and Table 2.

Figure 5:
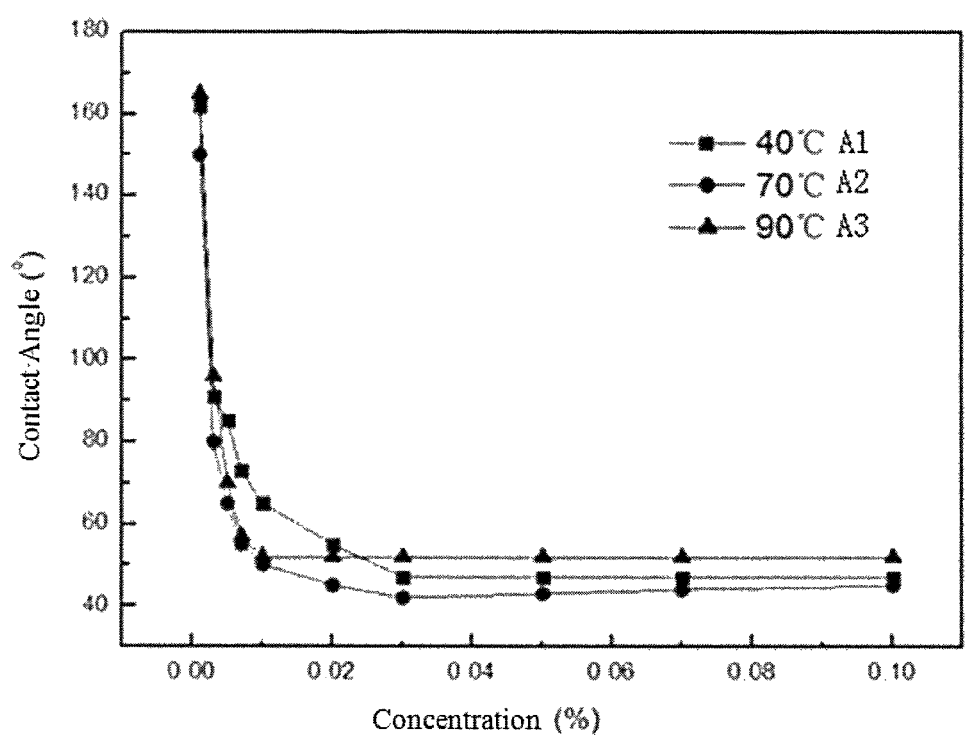
FIG. 5 shows the rock wettability of the solution of the fracturing and displacement fluid in examples 1-3 of the present invention after viscosity breaking.

(6) Rock Wettability of the Solutions of the Fracturing and Displacement Fluids after Viscosity Breaking Quartz plates (from Jiangsu Citotest Labware Manufacturing Co., Ltd., with trade name 80340-0130, the same below) are aged with a mixed solution of dehydrated crude oil and n-heptane (the volume ratio of dehydrated crude oil to n-heptane is 4:1) with the method specified in "Interaction between Asphaltene and Quartz Surface and Mechanisms of Wettability Alteration" (Yefei Wang, Suoliang Wang, Huaimin Xu, et al, Petroleum Geology and Recovery Efficiency, 2011, 18(4):72-74), the solutions obtained by respectively mixing fracturing and displacement fluids A1 and A4-A10 with water at 1:3 volume ratio at 40° C. for viscosity breaking are diluted to different concentrations (0.005 wt %, 0.01 wt %, 0.02 wt %, 0.05 wt %, and 0.10 wt %, the same below), and the contact angles of the solutions at different diluted concentrations acting on the surface of quartz plate are measured with the static contact angle measurement method specified in "SY/T5153.3-95 Measurement of Reservoir Rock Wettability—Contact Angle Method". The contact angle of the diluted fracturing and displacement fluid A1 after viscosity breaking is shown in FIG. 5 and Table 2, and the contact angles of the diluted fracturing and displacement fluids A4-A10 after viscosity breaking are shown in Table 2;

Quartz plates are aged with a mixed solution of dehydrated crude oil and n-heptane (the volume ratio of dehydrated crude oil to n-heptane is 4:1) with the method specified in "Interaction between Asphaltene and Quartz Surface and Mechanisms of Wettability Alteration" (Yefei Wang, Suoliang Wang, Huaimin Xu, et al, Petroleum Geology and Recovery Efficiency, 2011, 18(4):72-74), the solution obtained by mixing fracturing and displacement fluid A2 with water at 1:3 volume ratio at 70° C. for viscosity breaking is diluted to different concentrations, and then the contact angles of the solutions at different diluted concentrations acting on the surface of quartz plate are measured with the static contact angle measurement method specified in "SY/T5153.3-95 Measurement of Reservoir Rock Wettability—Contact Angle Method". The contact angle of the diluted fracturing and displacement fluid A2 after viscosity breaking is shown in FIG. 5 and Table 2;

Quartz plates are aged with a mixed solution of dehydrated crude oil and n-heptane (the volume ratio of dehydrated crude oil to n-heptane is 4:1) with the method specified in "Interaction between Asphaltene and Quartz Surface and Mechanisms of Wettability Alteration" (Yefei Wang, Suoliang Wang, Huaimin Xu, et al, Petroleum Geology and Recovery Efficiency, 2011, 18(4):72-74), the solution obtained by mixing fracturing and displacement fluid A3 with water at 1:3 volume ratio at 90° C. for viscosity breaking is diluted to different concentrations, and then the contact angles of the solutions at different diluted concentrations acting on the surface of quartz plate are measured with the static contact angle measurement method specified in "SY/T5153.3-95 Measurement of Reservoir Rock Wettability—Contact Angle Method". The contact angle of the diluted fracturing and displacement fluid A3 after viscosity breaking is shown in FIG. 5 and Table 2.

Figure 6:
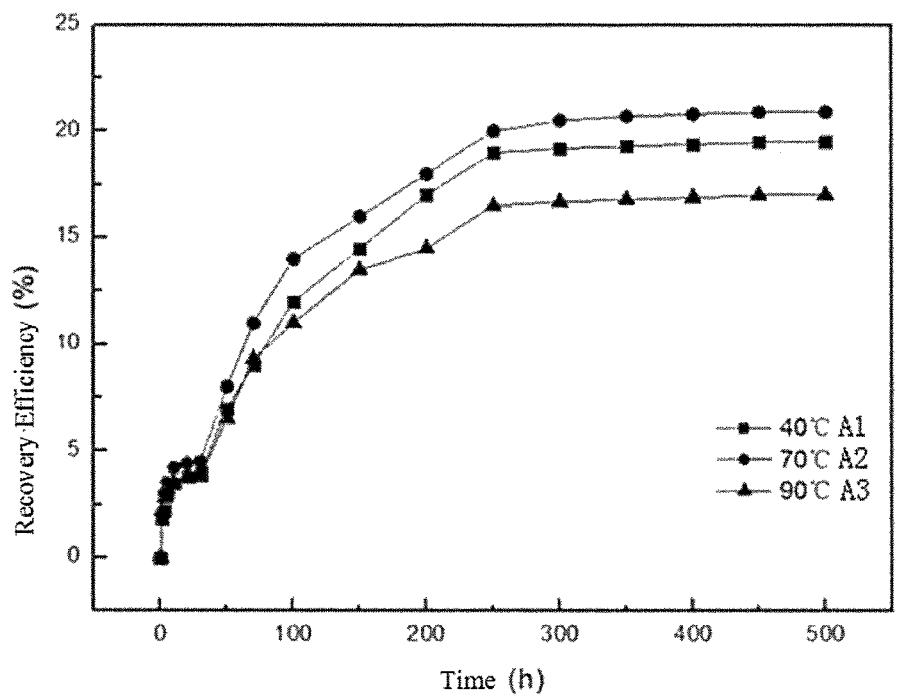
FIG. 6 shows the imbibition, drainage and oil displacement ability of the solution of the fracturing and displacement fluid in examples 1-3 of the present invention after viscosity breaking.
Figure 7:
FIG. 7 shows the imbibition, drainage and oil displacement effect of a dilute solution obtained by diluting the fracturing and displacement fluid in the example 2 of the present invention to 0.05 wt % concentration after viscosity breaking against degassed and dehydrated crude oil.

(7) Imbibition, Drainage and Oil Displacement Ability of the Solutions of Fracturing and Displacement Fluids after Viscosity Breaking Solutions obtained by mixing the fracturing and displacement fluids A1 and A4-A10 with water at 1:3 volume ratio at 40° C. for viscosity breaking are diluted to 0.05 wt % concentration respectively, and then the imbibition, drainage and oil displacement ability of the obtained dilute solutions in a rock core A (diameter=25 mm, length=31.2 mm, gas permeability=0.25 mD) at 40° C. is evaluated with the spontaneous imbibition method specified in "Experimental Study of Spontaneous Imbibition in Low Permeability Core, Fractured Reservoir" (Aifen Li, Tianyou Fan, and Lin Zhao, Petroleum Geology and Recovery Efficiency, 2011, 18(5): 67-69), and the imbibition recovery percentage (recovery efficiency) in 500 h is calculated. The result of the fracturing and displacement fluid A1 is shown in FIG. 6 and Table 2, and the results of the fracturing and displacement fluids A4-A10 are shown in Table 2;

A solution obtained by mixing the fracturing and displacement fluid A2 with water at 1:3 volume ratio at 70° C. for viscosity breaking is diluted to 0.05 wt % concentration respectively, and then the imbibition, drainage and oil displacement ability of the obtained dilute solution in a rock core B (diameter=24.9 mm, length=30.6 mm, gas permeability=0.23 mD) at 70° C. is evaluated with the spontaneous imbibition method specified in "Experimental Study of Spontaneous Imbibition in Low Permeability Core, Fractured Reservoir" (Aifen Li, Tianyou Fan, and Lin Zhao, Petroleum Geology and Recovery Efficiency, 2011, 18(5): 67-69), and the imbibition recovery percentage (recovery efficiency) in 500 h is calculated. The result is shown in FIGS. 6 and 7 and Table 2;

A solution obtained by mixing the fracturing and displacement fluid A3 with water at 1:3 volume ratio at 90° C. for viscosity breaking is diluted to 0.05 wt % concentration respectively, and then the imbibition, drainage and oil displacement ability of the obtained dilute solution in a rock core C (diameter=25 mm, length=30.8 mm, gas permeability=0.27 mD) at 90° C. is evaluated with the spontaneous imbibition method specified in "Experimental Study of Spontaneous Imbibition in Low Permeability Core, Fractured Reservoir" (Aifen Li, Tianyou Fan, and Lin Zhao, Petroleum Geology and Recovery Efficiency, 2011, 18(5): 67-69), and the imbibition recovery percentage (recovery efficiency) in 500 h is calculated. The result is shown in FIG. 6 and Table 2.

TABLE 1

| | Viscosity after shearing for 2 h/mPa · s | Average sedimentation velocity measured with falling ball method/mm/s | Viscosity of mixtures of crude oil and fracturing and displacement fluid mixed at different volume ratios after 2 h/mPa · s | | | Viscosity of mixtures of water and fracturing and displacement fluid mixed at different volume ratios after 2 h/mPa · s | | |
|---|---|---|---|---|---|---|---|---|
| | | | 1:5 | 2:5 | 3:5 | 3:1 | 4:1 | 5:1 |
| A1 | 58 | 0.64 | 4.0 | 3.0 | 2.1 | 4.8 | 4.0 | 3.0 |
| A2 | 60 | 0.66 | 4.3 | 3.7 | 2.6 | 4.8 | 3.9 | 2.9 |
| A3 | 70 | 0.57 | 4.5 | 3.8 | 2.7 | 4.9 | 3.8 | 2.8 |
| A4 | 56 | 0.66 | 4.5 | 3.3 | 2.4 | 4.8 | 4.0 | 3.0 |
| A5 | 53 | 0.67 | 4.6 | 3.4 | 2.1 | 4.7 | 3.8 | 2.8 |
| A6 | 54 | 0.65 | 4.6 | 3.3 | 2.1 | 4.7 | 3.7 | 2.7 |
| A7 | 55 | 0.68 | 4.5 | 3.1 | 2.0 | 4.9 | 4.0 | 3.1 |
| A8 | 51 | 0.68 | 4.3 | 3.2 | 2.0 | 4.5 | 3.6 | 2.7 |
| A9 | 52 | 0.69 | 4.2 | 3.0 | 2.1 | 4.6 | 3.7 | 2.7 |
| A10 | 51 | 0.69 | 3.9 | 2.9 | 1.9 | 4.4 | 3.5 | 2.5 |

Figure 2:
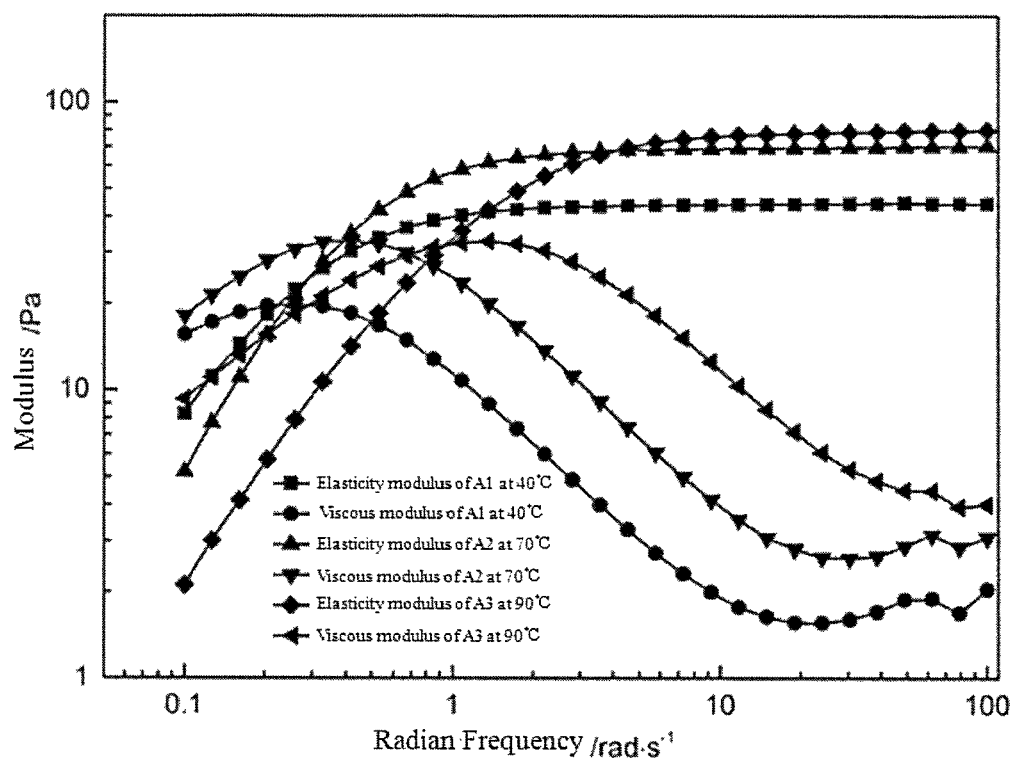
FIG. 2 shows the viscoelasticity of the fracturing and displacement fluid in examples 1-3 of the present invention.

It is seen from the viscosity after shearing for 2 h in FIG. 1 and Table 1: the viscosity of the fracturing and displacement fluids that contain the composition provided in the present invention at the formation temperature is still >50 mPa·s, and the fracturing and displacement fluids have good temperature-resistant and shearing-resistant properties, and meet the requirements specified in SY/T6376-2008 "General Technical Specifications of Fracturing Fluids"; it is seen from FIG. 2: the fracturing and displacement fluids that contain the composition provided in the present invention have good viscoelasticity; it is seen from the sedimentation velocity data measured with a falling ball method in FIG. 3 and Table 1: the sedimentation velocity of the fracturing and displacement fluids that contain the composition provided in the present invention is lower than 0.7 mm/s, much lower than the sedimentation velocity (greater than 10 mm/s) of guar gum fracturing fluid, and exhibits stronger solid carrying ability; it is seen from the viscosity data of the mixtures of crude oil/water and fracturing and displacement fluids mixed at different mix ratios after 2 h: the viscosity of the fracturing and displacement fluids that contain the composition provided in the present invention after the fracturing operation is greatly decreased within 2 h after the fracturing and displacement fluids encountering crude oil or water in the formation and viscosity breaking happens, the viscosity of the fracturing and displacement fluids is <5 mPa·s, and the viscosity breaking performance is good.

It is seen from the oil-water interfacial tension data of the solutions of fracturing and displacement fluids at different diluted concentrations after viscosity breaking: the oil-water interfacial tension is at an ultra-low level within a wide range, preferably the oil-water interfacial tension is at $10^{-3}$ mN/m level, which demonstrates that the fracturing and displacement fluids have superior oil-water interfacial tension reduction ability; it is seen from the contact angle data of the solutions of fracturing and displacement fluid at different diluted concentrations after viscosity breaking in FIG. 5 and Table 2: the dilute solution after viscosity breaking enhances hydrophilicity of the surface of quartz plate within a wide concentration range and converts the oleophilic surface into a hydrophilic surface, the contact angle is smaller than 90°, and is 43° at the minimum, which is beneficial for imbibition, drainage and oil displacement; it is seen from the recovery efficiency data in FIGS. 6 and 7 and Table 2: the imbibition recovery percentage of the rock core is >15%, which demonstrates that the fracturing and displacement fluid has good performance in imbibition and oil displacement and is beneficial for improving recovery efficiency of tight oil significantly.

While the present invention is described above in details in some preferred embodiments, the present invention is not limited to those embodiments. Various simple variations, including combinations of the technical features in any other appropriate way, can be made to the technical scheme of the present invention within the scope of the technical concept

TABLE 2

Oil-water interfacial tension (mN/m) and contact angle (°) of solutions of fracturing and displacement fluids at different diluted concentrations after viscosity breaking

| | 0.005 wt % | | 0.01 wt % | | 0.02 wt % | | 0.05 wt % | | 0.10 wt % | | |
|---|---|---|---|---|---|---|---|---|---|---|---|
| | Oil-water interfacial tension | Contact angle | Oil-water interfacial tension | Contact angle | Oil-water interfacial tension | Contact angle | Oil-water interfacial tension | Contact angle | Oil-water interfacial tension | Contact angle | Recovery efficiency/% |
| A1 | 0.0115 | 85.4 | 0.0068 | 65.0 | 0.0100 | 55.2 | 0.0210 | 47.5 | 0.0195 | 47.5 | 19.5 |
| A2 | 0.0087 | 65.5 | 0.0048 | 50.6 | 0.0122 | 45.3 | 0.0155 | 43.5 | 0.0155 | 45.2 | 20.9 |
| A3 | 0.0902 | 70.4 | 0.0058 | 52.8 | 0.0185 | 52.1 | 0.0295 | 52.4 | 0.0293 | 52.6 | 17.0 |
| A4 | 0.0125 | 88.2 | 0.0106 | 77.6 | 0.0136 | 65.3 | 0.0159 | 58.6 | 0.0188 | 56.4 | 16.7 |
| A5 | 0.0177 | 89.6 | 0.0123 | 80.5 | 0.0188 | 71.2 | 0.0211 | 62.8 | 0.0266 | 56.6 | 17.9 |
| A6 | 0.0168 | 87.9 | 0.0102 | 81.2 | 0.0168 | 70.3 | 0.0198 | 65.3 | 0.0223 | 58.8 | 15.2 |
| A7 | 0.0155 | 88.7 | 0.0166 | 83.5 | 0.0188 | 69.7 | 0.0233 | 64.9 | 0.0244 | 60.9 | 16.0 |
| A8 | 0.0211 | 86.5 | 0.0196 | 80.1 | 0.0248 | 74.5 | 0.0267 | 70.6 | 0.0299 | 66.2 | 17.5 |
| A9 | 0.0235 | 88.4 | 0.0199 | 80.2 | 0.0238 | 76.2 | 0.0299 | 68.5 | 0.0302 | 62.7 | 17.4 |
| A10 | 0.0315 | 88.1 | 0.0267 | 83.6 | 0.0335 | 73.8 | 0.0410 | 69.6 | 0.0498 | 65.4 | 15.1 |

The invention claimed is:

1. A composition for fracturing and displacement, the composition consisting of an aqueous solution of a pyrrolic compound represented by formula (1) and a laurate;

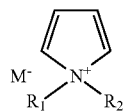

formula (1)

wherein M⁻ is halide ion, $R_1$ is C1-C3 linear alkyl, and $R_2$ is C17-C19 linear alkyl;
wherein the laurate is selected from sodium laurate, potassium laurate, and combinations thereof,
wherein the pyrrolic compound is present in an amount of 0.5 wt % to 10 wt % and the laurate is present in an amount of 0.1 wt % to 2 wt %.

2. The composition according to claim 1, wherein, M⁻ is bromine ion, $R_1$ is methyl, and $R_2$ is octadecyl.

3. The composition according to claim 1, wherein, a weight ratio of the pyrrolic compound to the laurate contained is 0.5-20:1.

4. The composition according to claim 1, wherein water used to form the aqueous solution contains $Na^+$, $K^+$, $Ca^{2+}$, $Mg^{2+}$, $HCO_3$ and $Cl^-$, wherein, the total concentration of $K^+$ and $Na^+$ is 1,000 mg/L to 100,000 mg/L, and the total concentration of $Ca^{2+}$ and $Mg^{2+}$ is 10 mg/L to 5,000 mg/L.

* * * * *